(12) United States Patent
Hauer-Jensen et al.

(10) Patent No.: US 6,540,976 B1
(45) Date of Patent: Apr. 1, 2003

(54) METHOD FOR REDUCING RADIATION TOXICITY

(75) Inventors: Martin Hauer-Jensen, Little Rock, AR (US); Paivi Aho, Helsinki (FI)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 398 days.

(21) Appl. No.: 09/159,334

(22) Filed: Sep. 23, 1998

Related U.S. Application Data (60) Provisional application No. 60/059,766, filed on Sep. 23, 1997, and provisional application No. 60/069,708, filed on Dec. 16, 1997.

(51) Int. Cl.[7] .............................................. A61K 49/00
(52) U.S. Cl. ....................... 424/9.1; 424/1.11; 424/1.65
(58) Field of Search ................................ 424/1.11, 1.65, 424/9.1, 9.3, 9.4, 9.5, 9.6, 9.7, 9.8; 562/1, 400; 568/18, 303, 20, 23, 38; 564/502, 127, 128; 514/520; 430/944

(56) References Cited

U.S. PATENT DOCUMENTS

| | | | | |
|---|---|---|---|---|
| 5,185,370 A | * | 2/1993 | Backström et al. | ......... 514/520 |
| 5,292,771 A | * | 3/1994 | Backström et al. | ......... 514/472 |

FOREIGN PATENT DOCUMENTS

| | | | |
|---|---|---|---|
| WO | 8900165 | * | 1/1989 |

* cited by examiner

*Primary Examiner*—Dameron L. Jones
(74) *Attorney, Agent, or Firm*—Benjamin Aaron Adler (57) ABSTRACT

Intestinal radiation injury (radiation enteropathy) is an important dose limiting factor during treatment of abdominal and pelvic tumors and a major determinant in the quality of life among cancer survivors. Inflammatory and fibrogenic mediators released by mucosal inflammatory cells are involved in the mechanisms of injury. Treatment with Orazipone decreases the toxicity following Gy radiation dose, as measured by histopathologic scoring, TGF-$\beta$, IL-1$\alpha$, and ED-2 macrophage antigen immunoreactivity.

6 Claims, 10 Drawing Sheets

METHOD FOR REDUCING RADIATION TOXICITY

CROSS-REFERENCE TO RELATED APPLICATION

This non-provisional patent application claims benefit of provisional patent application U.S. Serial No. 60/059,766, filed Sep. 23, 1997 and provisional patent application U.S. Serial No. 60/069,708, filed Dec. 16, 1997, now abandoned.

BACKGROUND OF THE INVENTION

1. Field of the Invention

The present invention relates generally to the field of radiation therapy. More specifically, the present invention relates to a method for treatment of toxicity due to radiation therapy.

2. Description of the Related Art

Radiation therapy is an important strategy in the treatment of many cancers. The use of external beam radiation therapy has produced curative treatment programs for several tumor types. However, this technique has practical limitations in regards to the field of therapy, radioresistance mechanisms, and normal tissue toxicity. The risk of chronic intestinal toxicity (radiation enteropathy) is the main dose-limiting factor during abdominal radiation therapy and is a major determinant in the quality of life in cancer survivors.

Inflammatory and fibrogenic mediators released by mucosal inflammatory cells are involved in the mechanisms of toxicity. The pathophysiological mechanisms of the toxicity may include mucosal barrier break-down, extracellular matrix deposition or intraluminal factors. Chronic enteropathy may be due to endothelial dysfunction, chronic inflammation, or an oxidative imbalance. Attempts to prevent radiation enteropathy by reducing the dose to volume ratio include abdominopelvic partitioning or patient positioning such as using a belly-board. To date, treatment for radiation enteropathy is limited to pharmacologic-dietary intervention methods to try to interfere with or modulate the normal tissue response.

In the clinical situation, radiation therapy is usually not administered as a single dose, but as multiple daily fractions, primarily because the dose-response curve with fractionated radiation is less steep than for single dose radiation. Also, fractionated radiation is associated with what can be regarded as a "fractionated immune response". For these reasons, radioprotectors that show protection with single dose radiation sometimes do not show significant protection when tested with fractionated radiation.

Thus, the prior art is deficient in preventing radiation enteropathy following radiation treatments for cancer, and in treating the disorder once it occurs. This deficiency has resulted in limited doses of radiation therapy administered to cancer patients. The present invention fulfills this long-standing need and desire in the art.

SUMMARY OF THE INVENTION

The present invention describes the use of orazipone for ameliorating intestinal radiation toxicity. Results presented herein suggest that administration of orazipone prior to, during and after small bowel irradiation effectively reduces radiation-induced histopathologic injury, inflammation, and TGF-β overexpression.

Previous attempts at identifying radioprotective agents for clinical use have been largely hampered by a) toxicity, b) issues of possible tumor protection, and/or c) unfavorable price/efficacy ratio. Strategies to ameliorate radiation enteropathy have been under investigation for some time. One approach has been to interfere with the mechanism of injury by eliminating reactive oxygen species, inhibiting apoptosis, and/or stimulating DNA repair. Another approach has been to interfere with the normal tissue response to try to abrogate tissue injury and/or increase tolerance.

The advantages of the drug, orazipone, are that it is active locally and is administered directly into the intestine. The small amounts that are absorbed are rapidly broken down to inactive metabolites. Toxicity at effective dose levels is thus minimal, and tumor protection is not an issue (with the possible exception of intestinal tumors).

One object of the present invention is to provide a method for the prevention and/or treatment of radiation enteropathy.

One embodiment of the present invention provides a drug to be administered locally to ameliorate radiation toxicity, such as, enteropathy in a patient in need of such treatment.

In yet another embodiment of the present invention, there is provided a drug to be administered locally for a period of time prior to, during and following therapeutic radiation which decreases and/or prevents the radiation toxicity in a patient suffering from cancer.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 7 shows 'late' vs. 'early' administration of Orazipone following fractionated radiation on (FIG. 7A) Radiation Injury Score; (FIG. 7B) TGF-β immunoreactivity; (FIG. 7C) intestinal wall thickness; and (FIG. 7D) mucosal surface area.

DETAILED DESCRIPTION OF THE INVENTION

Figure 1:
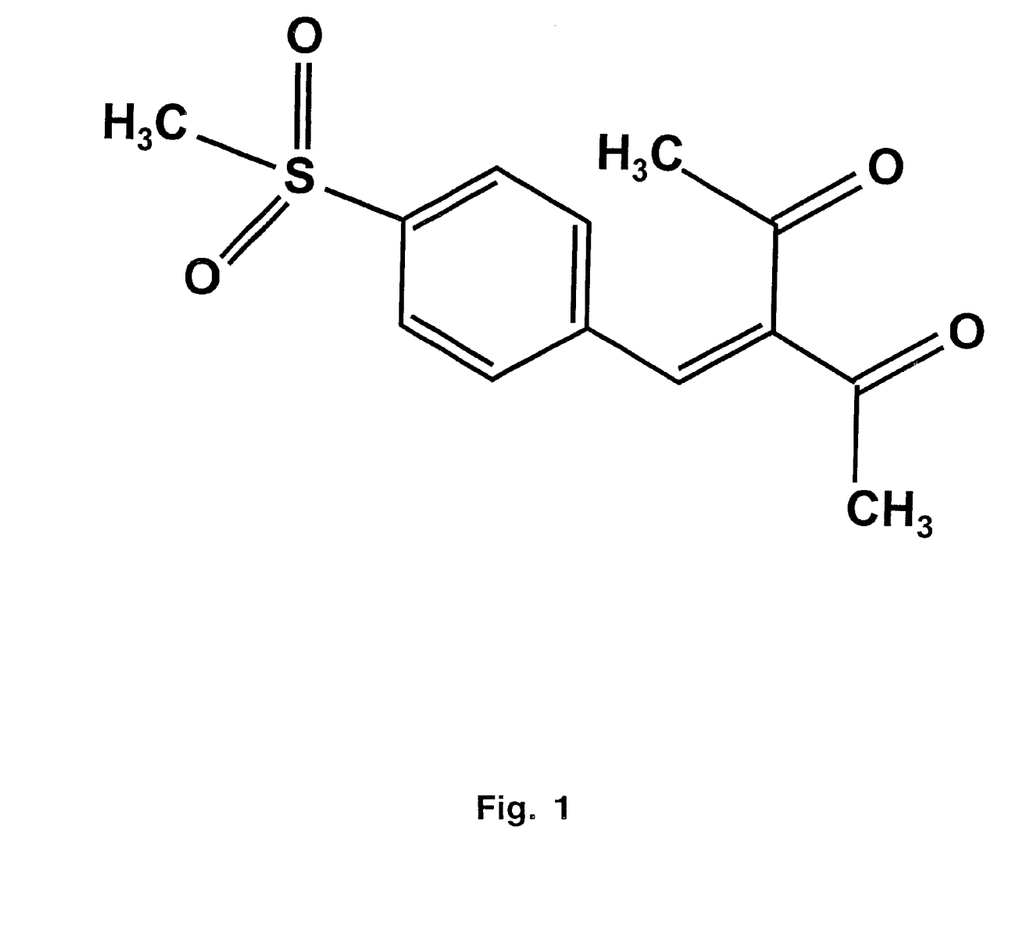
FIG. 1 shows the structure of Orazipone.
Figure 2:
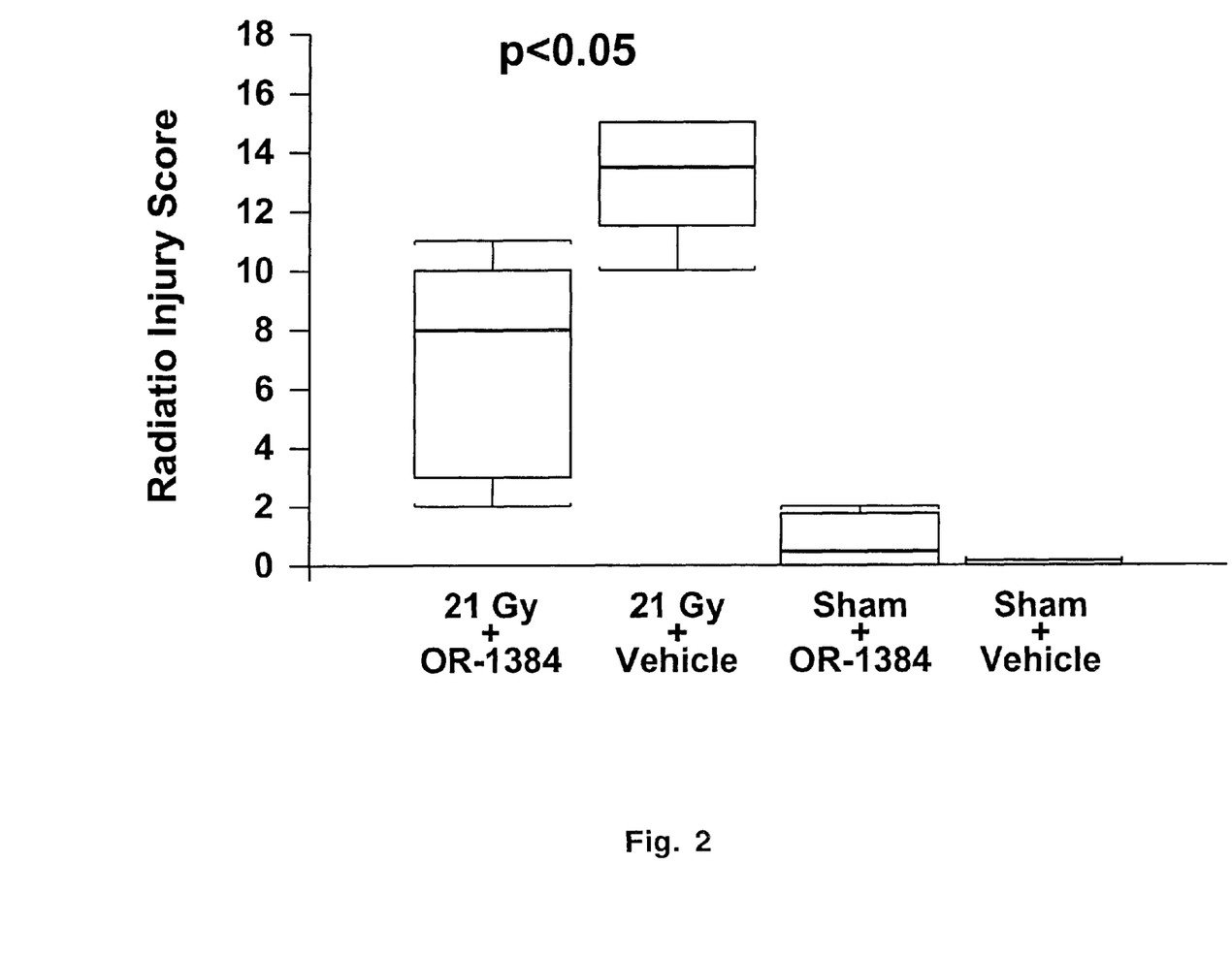
FIG. 2 shows the radiation injury score two weeks after single dose irradiation.
Figure 3:
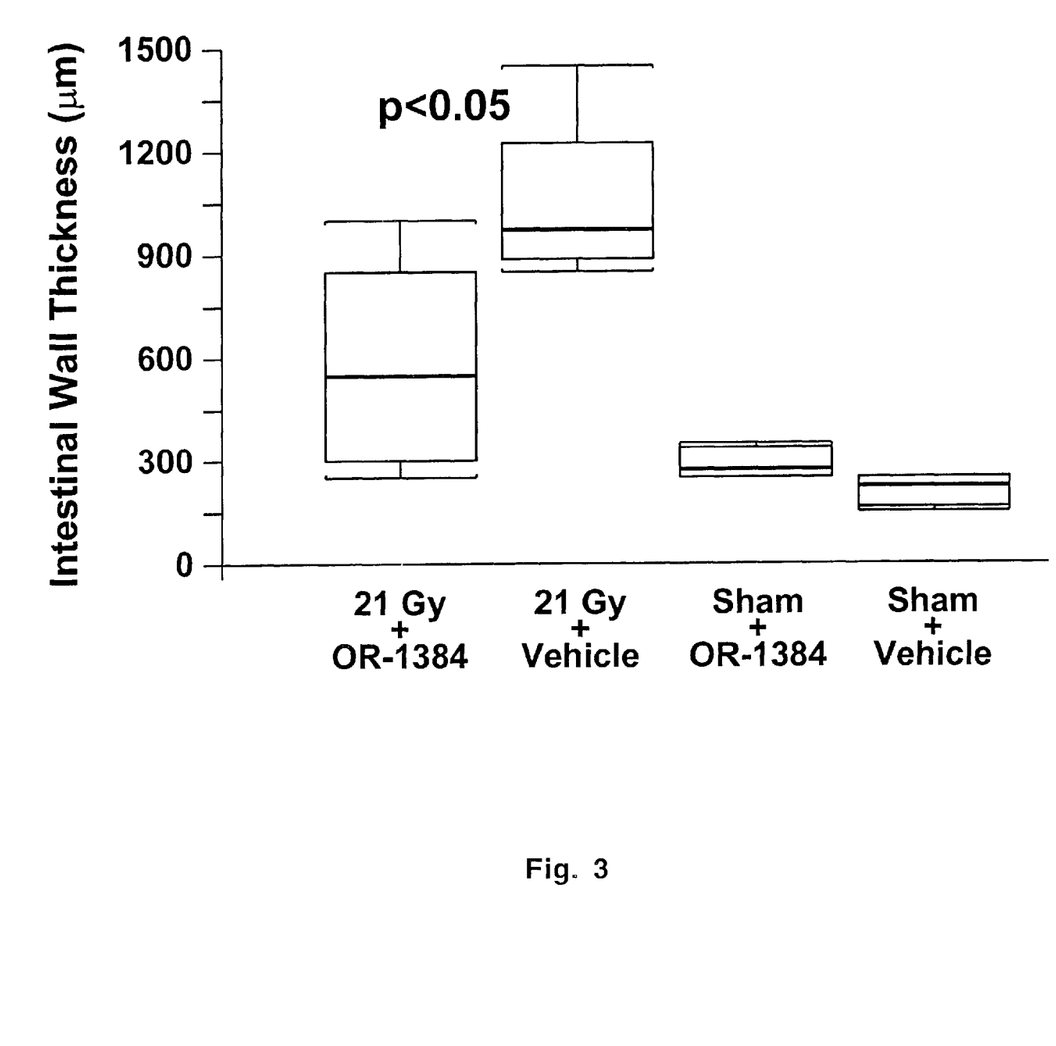
FIG. 3 shows the intestinal wall thickness two weeks after single dose irradiation.
Figure 4:
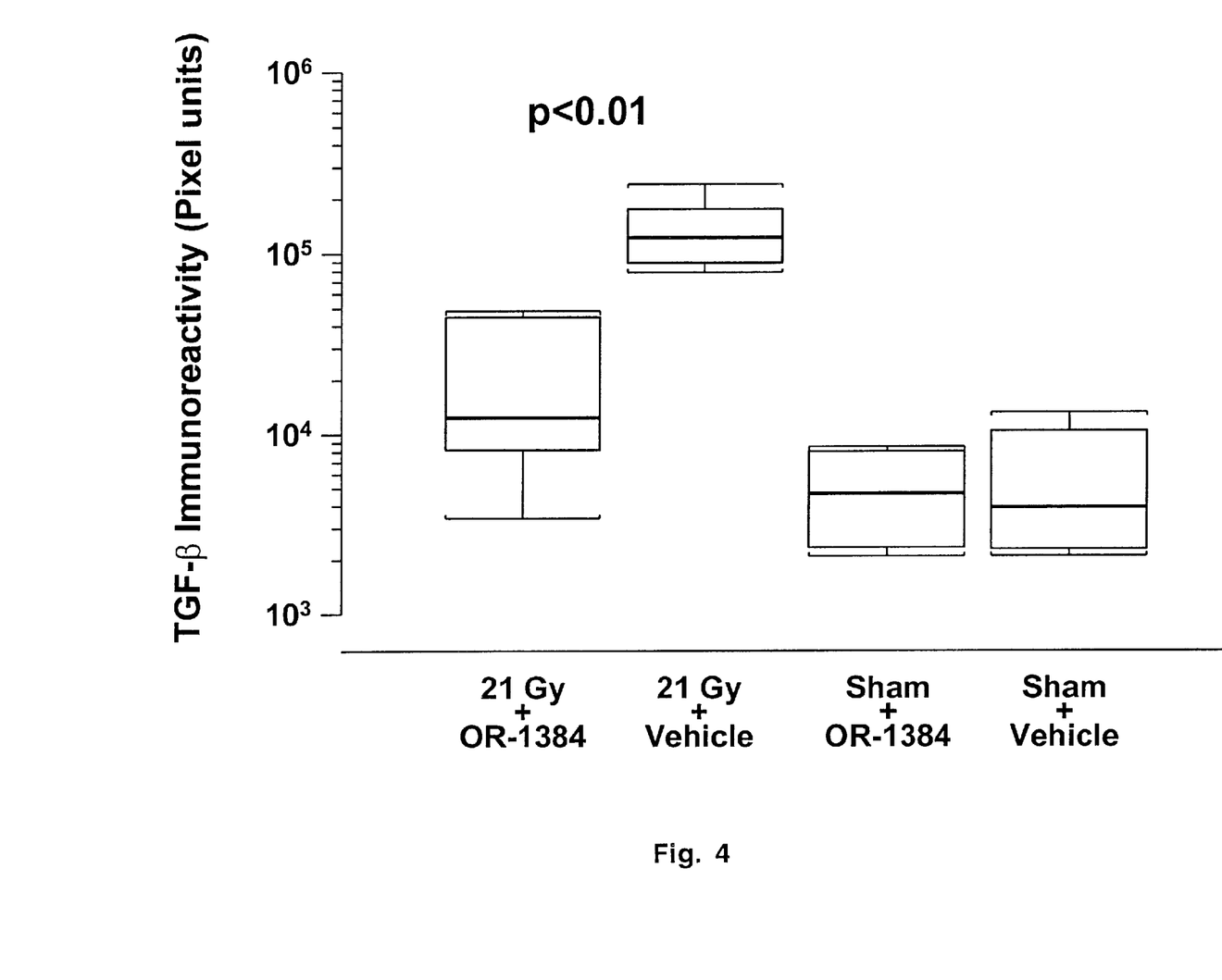
FIG. 4 shows the intestinal wall TGF-β immunoreactivity levels two weeks after single dose irradiation.
Figure 5:
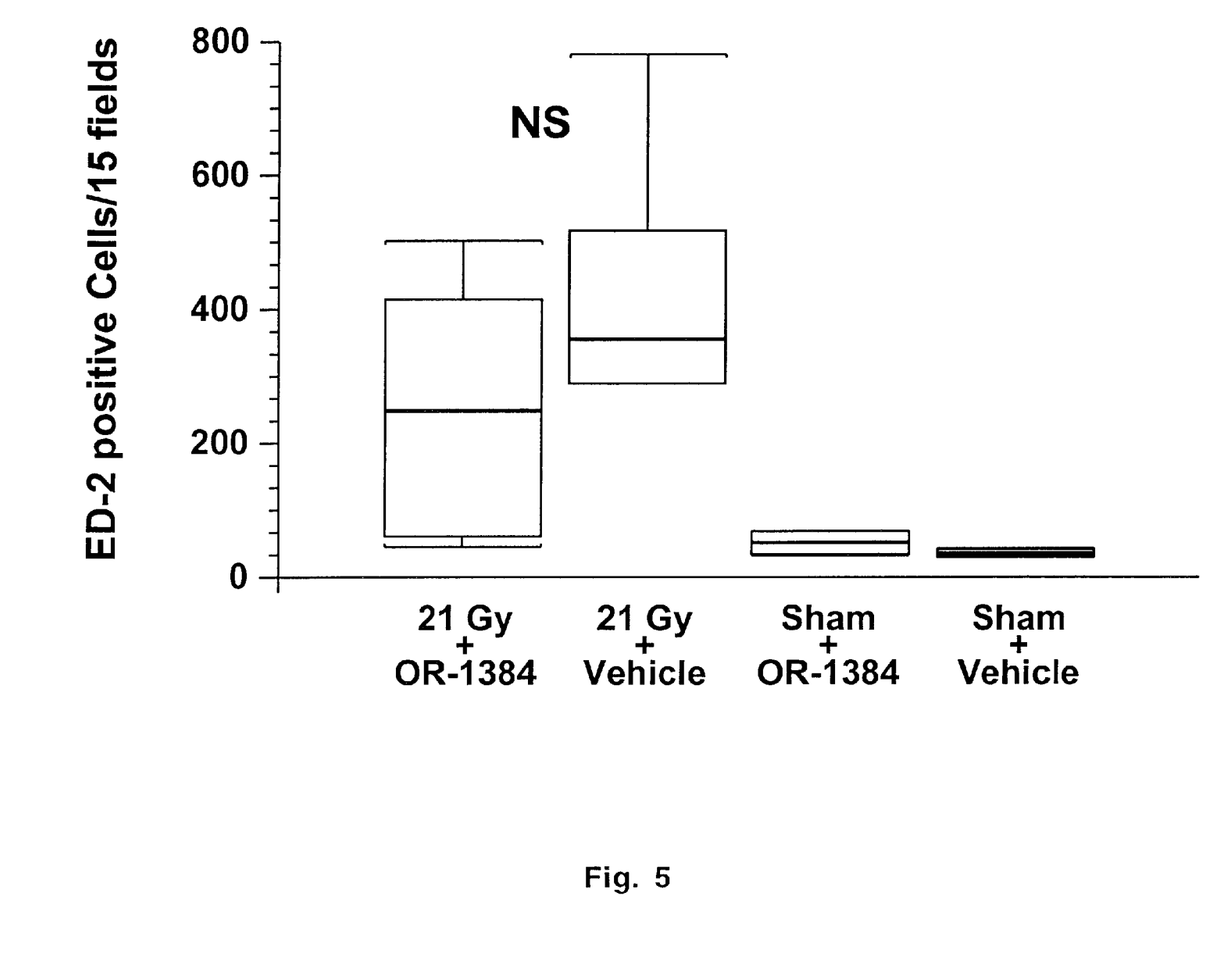
FIG. 5 shows the number of ED-2 positive cells two weeks after single dose irradiation.
Figure 6:
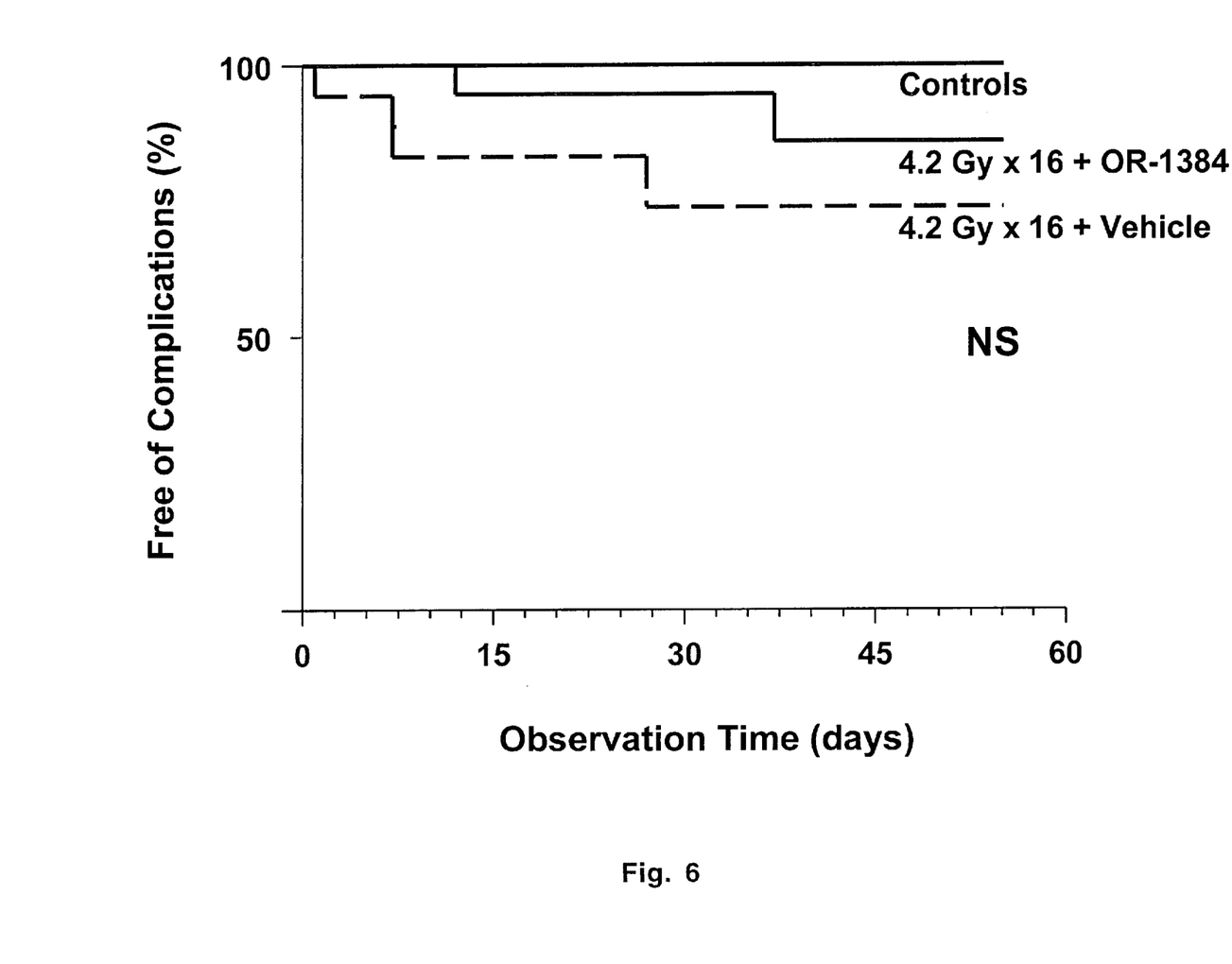
FIG. 6 shows the actuarial incidence of radiation-induced complications (intestinal obstruction or enterocutaneous fistula formation).
Figure 7A:
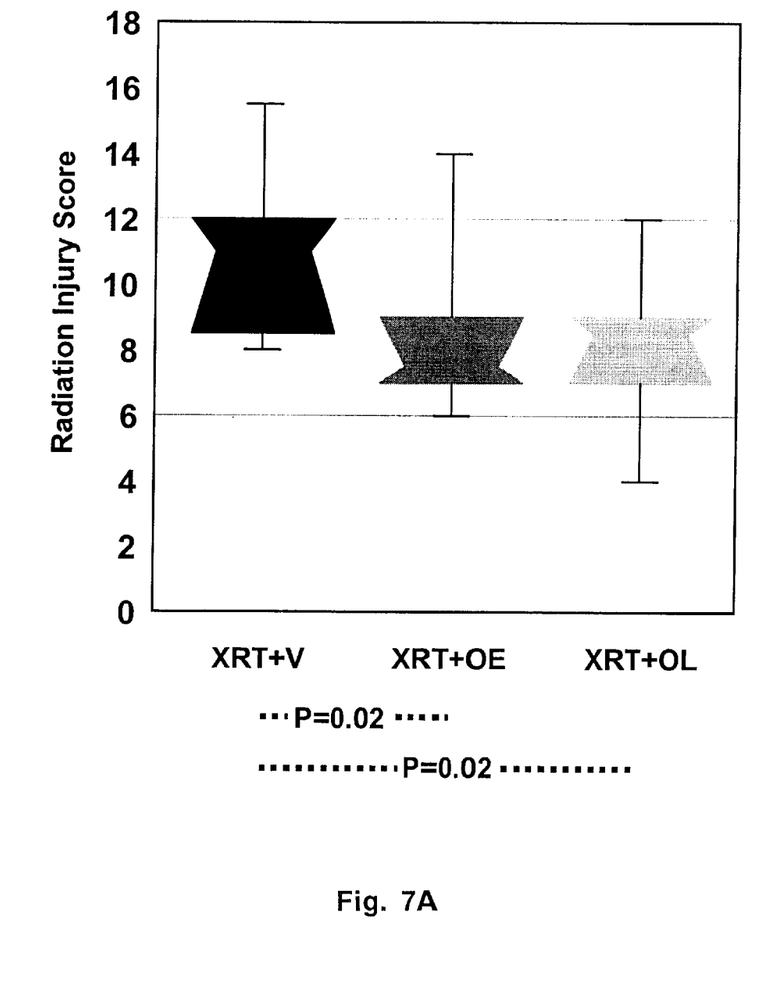
Figure 7B:
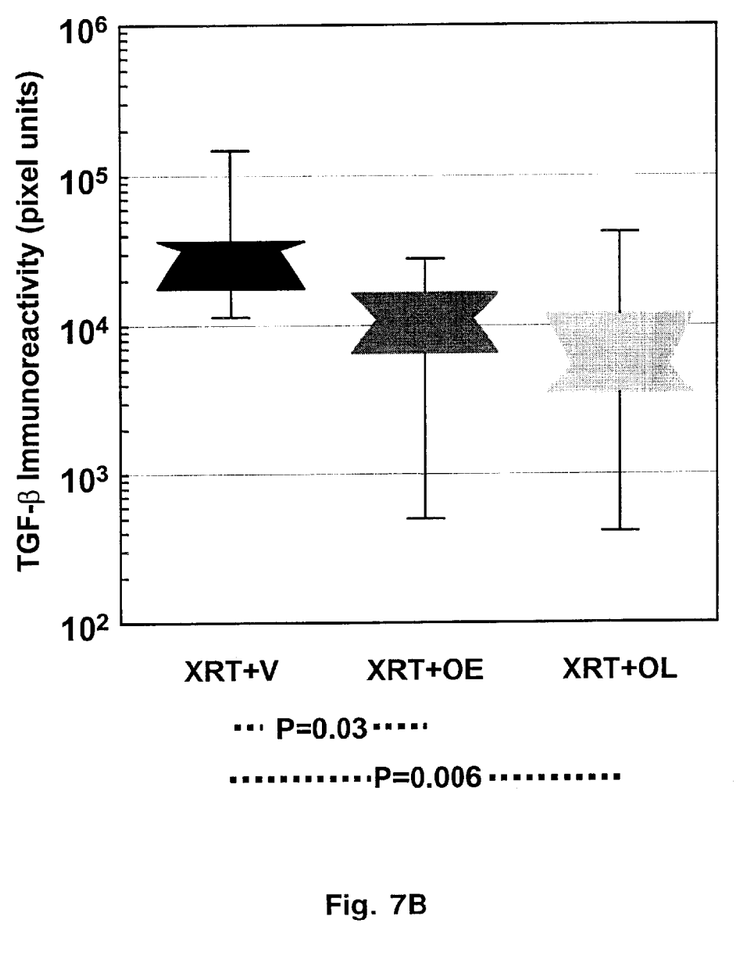
Figure 7C:
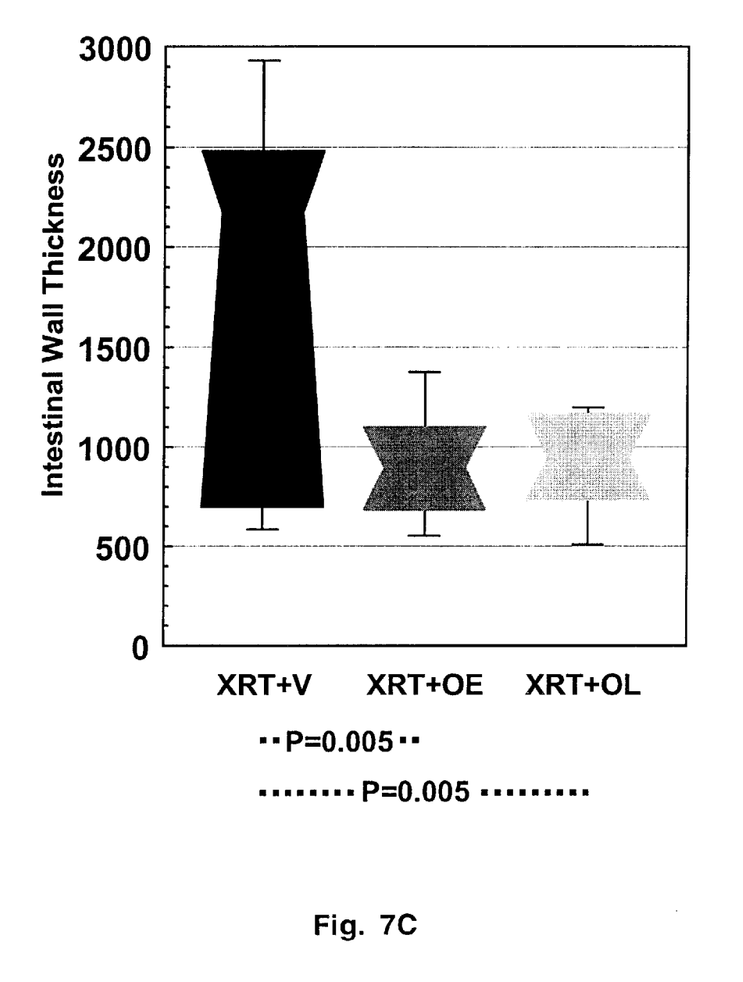
Figure 7D:
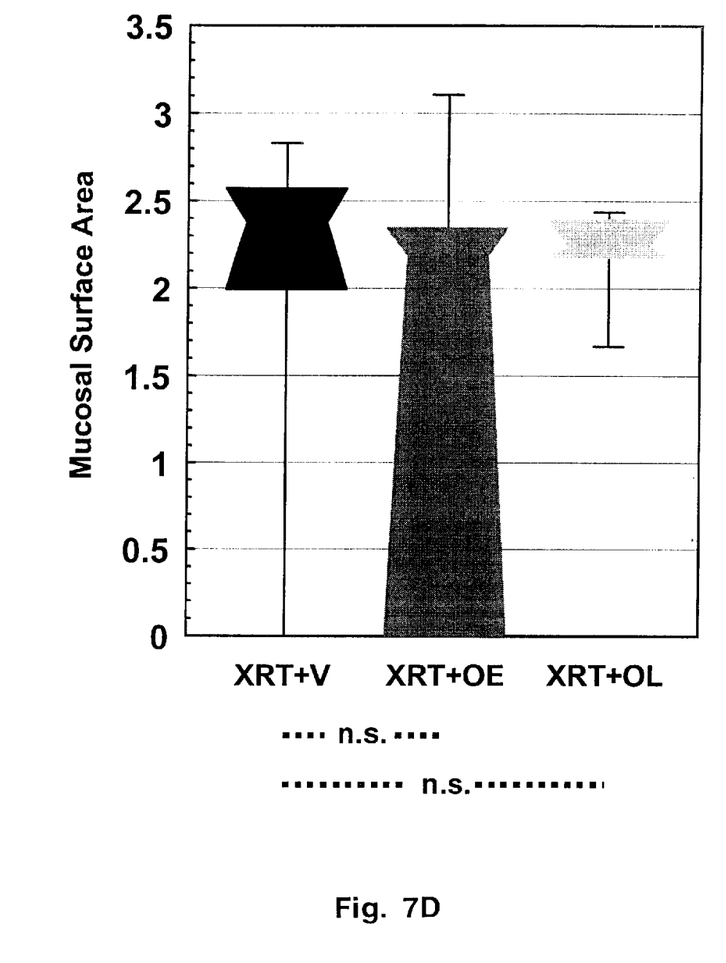

OR-1384, or Orazipone, is a low molecular weight ($M_w$265.22), locally acting immunomodulator, that forms reversible conjugates with thiol-groups. Orazipone inhibits the release of IL-1α, IL-1β and TNFα from mononuclear cells, suppresses NADPH oxidase and LTB$_4$ production by neutrophils, and reduces T-cell proliferation and IL-2 release. Orazipone also inhibits cytokine production.

The systemic effects of Orazipone are limited, as the drug is absorbed and broken down into inactive metabolites very quickly. Orazipone is currently undergoing Phase I/II testing by Orion Pharma in Finland in patients with inflammatory bowel disease. Radiation enteropathy has several features in common with chronic inflammatory bowel disease in terms of structural and functional alterations, as well as cellular and molecular mechanisms.

The present invention is directed towards a method of preventing and treating radiation enteropathy following radiation therapy for cancer. It is specifically contemplated that pharmaceutical compositions may be prepared using the application for Orazipone of the present invention. In such a case, the pharmaceutical composition comprises the Orazipone of the present invention and a pharmaceutically acceptable carrier. A person having ordinary skill in this art would readily be able to determine, without undue experimentation, the appropriate dosages and routes of administration of Orazipone.

When used in vivo for therapy, the drug of the present invention is administered to the patient or an animal in therapeutically effective amounts, i.e., amounts that eliminate or reduce the toxicity during and following radiation therapy. It may be administered in a solid or liquid form. For example, it may be administered orally, preferably in an enterosoluble preparation, or rectally in a suppository or in an enema. The dose and dosage regimen of Orazipone will depend upon the radiation dose(s) being administered to the patient e.g., the therapeutic index, the patient, the patient's history and other factors. A single dose of Orazipone administered will typically be in the range of about 0.05 to about 5 mg/kg of patient weight, whereas the typical single dose for small animals such as dog and cat will be somewhat higher, i.e. in the range of about 1 to about 50 mg/kg of body weight. The dose and dosing schedule of Orazipone can be optimized for effectiveness while balanced against negative effects of treatment. See *Remington's Pharmaceutical Science*, 17th Ed. (1990) Mark Publishing Co., Easton, Pa.; and *Goodman and Gilman's: The Pharmacological Basis of Therapeutics*, 8th Ed (1990) Pergamon Press; which are incorporated herein by reference. Examples of pharmaceutically acceptable carriers are water, saline, Ringer's solution, dextrose solution, and 5% human serum albumin. Nonaqueous vehicles such as fixed oils and ethyl oleate may also be used. Liposomes may be used as carriers. The pharmaceutical composition may contain minor amounts of additives such as substances that enhance isotonicity and chemical stability, e.g., buffers and preservatives. Orazipone will typically be formulated in such vehicles at concentrations of about 0.001 mg/ml to 100 mg/ml such that the final dose is about 0.05 to 5 mg/kg of patient body weight or about 1 to 50 mg/kg of animal (i.e. dog, cat, etc.) body weight.

The following examples are given for the purpose of illustrating various embodiments of the invention and are not meant to limit the present invention in any fashion:

EXAMPLE 1

Methods

A 4-cm segment of distal ileum was sutured to the inside of the scrotum in orchiectomized male rats, thus forming an artificial "scrotal hernia". The afferent bowel was divided 10 cm proximal to the "hernia", an end ileostomy was prepared, and intestinal continuity was restored by end-to-side anastomosis. The intestine in the "hernia" was subsequently exposed to 0, 18, or 21 Gy single dose, or 8 daily fractions of 5.6 Gy (total dose 44.8 Gy), external beam X-irradiation. Orazipone or vehicle was injected through the stoma from 3 days prior to 2 weeks after irradiation. Mucosal injury was monitored non-invasively by assessment of granulocyte marker protein (GMP) excretion. Irradiated and shielded intestine were procured 2 weeks after irradiation and assessed for structural changes by histopathologic scoring, and for TGF-β, IL-1α, and ED-2 macrophage antigen immunoreactivity. Radiation injury scores are Ad the sum of 7 different histopathologic parameters graded according to severity. Intestinal wall thickness was measured with light microscopy and a stage micrometer. Intestinal wall TGF-β immunoreactivity levels were measured with computerized image analysis, and the number of ED-2 positive cells (macrophages) were counted with a light microscope and fields were determined according to a predetermined grid pattern.

EXAMPLE 2

Effects of Orazipone Following Single Dose Radiation

The present invention shows that a single dose of Orazipone at a concentration of 30 mg/kg reduced the frequency of subacute severe small bowel radiation toxicity from 80% to 25% and significantly attenuated TGF-β overexpression when administered daily for 1 week after a single dose of 21 Gy. Overall, irradiated intestine from Orazipone-treated rats exhibited less histopathologic injury ($p<0.01$), intestinal wall thickening ($p<0.05$), extracellular matrix-associated TGF-β immunoreactivity ($p<0.01$), and IL-1α positive cells ($p=0.05$), compared to vehicle-treated controls. GMP excretion and macrophage accumulation were not significantly affected by Orazipone administration.

There was a large difference in the degree of serosal thickening/fibrosis in the ulcerated areas. This is where the most TGF-β and lesions are normally observed, which are probably responsible for the "consequential" late effects. The "consequential" late effects are primarily responsible for the clinical complications that occur in patients.

EXAMPLE 3

Effects of Orazipone Following Fractionated Radiation

To evaluate the effects of Orazipone following fractionated radiation, the transposed loop of small bowel was exposed to sham-irradiation or 8 daily fractions of 5.6 Gy (total dose 44.8 Gy). Orazipone (30 mg/kg q.d.) or vehicle was delivered for 14 days in 2 separate experimental groups. Group 1 received the drug during and after irradiation (radiation day 2 through post-radiation day 7), while Group 2 received the drug only after irradiation (post-radiation days 0 through 13). All animals were euthanized on post-radiation day 14.

Analysis of the data revealed that Orazipone (when given either during or after irradiation) significantly ameliorated subacute radiation enteropathy as assessed by Radiation Injury Score, intestinal wall thickness, and extracellular matrix-associated TGF-β immunoreactivity. However, the extent of mucosal injury (assessed by mucosal surface area measurements) did not differ among the treatment groups.

Thus, the present invention is directed to a method for the treatment of radiation enteropathy in a patient in need of such treatment, comprising the step of administering a therapeutically effective dose of Orazipone in a pharmacologically acceptable form to said patient. In general, the Orazipone is administered locally to affected area of said patient. Preferably, the area is selected from the group consisting of the abdomen, the intestine and the bowel.

Generally, the Orazipone is administered in any dose which has a palliative effect on radiation enteropathy. Preferably, the Orazipone is administered in a dose of from about 0.05 mg/kg to about 5 mg/kg.

Generally, the Orazipone may be administered in any route allowing it to have a palliative effect on radiation enteropathy. It may be administered in a solid or liquid form. For example, it may be administered orally, preferably in an enterosoluble preparation, or rectally in a suppository or in an enema.

The present invention is also directed to a method for the prevention of radiation enteropathy in a patient in need of such prevention, wherein said patient is being treated with radiation therapy for cancer, comprising the steps of: administering a therapeutic dose of Orazipone in a pharmacologically acceptable form locally to affected areas in said patient prior to or during said radiation therapy; and administering a therapeutic dose of Orazipone in a pharmacologically acceptable form locally to affected areas in said patient prior to, during, and/or subsequent to said radiation therapy. Preferably, the area is selected from the group consisting of the abdomen, the intestine and the bowel. More preferably, the route of administration can be either orally, preferably in an enterosoluble preparation, or rectally in a suppository or in an enema.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for the treatment of radiation enteropathy in a patient or an animal in need of such treatment, comprising the step of:
   administering a therapeutically effective dose of Orazipone in a pharmacologically acceptable form to said patient.

2. The method of claim 1, wherein said Orazipone is administered locally to an enteropathic area of said patient.

3. The method of claim 2, wherein said area is selected from the group consisting of the abdomen, the intestine and the bowel.

4. The method of claim 1, wherein said Orazipone is administered to a patient in a dose of from about 0.05 mg/kg to about 5 mg/kg.

5. The method of claim 1, wherein said Orazipone is administered orally or rectally.

6. The method of claim 1, wherein said administration of Orazipone is prior to radiation therapy, during radiation therapy or subsequent to radiation therapy.

* * * * *